United States Patent [19]

Guenther et al.

[11] Patent Number: 4,807,272

[45] Date of Patent: * Feb. 21, 1989

[54] X-RAY EQUIPMENT SUPPORT APPARATUS

[75] Inventors: Werner Guenther; Erich Heubeck, both of Bensheim, Fed. Rep. of Germany

[73] Assignee: Siemens Aktiengesellschaft, Berlin and Munich, Fed. Rep. of Germany

[ * ] Notice: The portion of the term of this patent subsequent to Jan. 31, 2006 has been disclaimed.

[21] Appl. No.: 845,688

[22] Filed: Mar. 28, 1986

[30] Foreign Application Priority Data

Apr. 1, 1985 [DE] Fed. Rep. of Germany ....... 3511876

[51] Int. Cl.$^4$ ............................ A61B 6/00; A61B 6/14; F16M 11/00; H05G 1/02
[52] U.S. Cl. .................................. 378/196; 248/123.1; 248/125; 378/197
[58] Field of Search .................... 378/39, 40, 194, 196, 378/197, 198; 248/123.1, 125, 297.1, 297.2, 165

[56] References Cited

U.S. PATENT DOCUMENTS

| 1,791,006 | 2/1931 | Shorr ................................ 248/297.2 |
| 2,369,453 | 2/1945 | Goldfield et al. . |
| 3,467,352 | 9/1969 | Bohler ................................ 248/125 |
| 3,496,354 | 2/1970 | Forsyth ............................. 378/197 |
| 3,530,293 | 9/1970 | Wehmer ............................. 378/196 |
| 3,536,913 | 10/1970 | Huchel ................................. 378/40 |
| 3,575,368 | 4/1971 | Thomas et al. . |
| 3,617,742 | 11/1971 | Schulman et al. . |
| 3,672,620 | 6/1972 | Fink ................................... 248/125 |
| 4,605,189 | 8/1986 | Bruneau .......................... 248/123.1 |

FOREIGN PATENT DOCUMENTS 201217  1/1966  Sweden .
746599  3/1956  United Kingdom .

OTHER PUBLICATIONS

Brochure M-D 80.1361 Orthopanto-Mograph 10; WS 08832.

Primary Examiner—Craig E. Church
Assistant Examiner—T. N. Grigsby

[57] ABSTRACT

In medical, particularly dental medical apparatus which comprise a stationarily erectible post at which a carriage is adjustably held by means of a guidance device as a carrier of a medical apparatus, for example an X-ray apparatus, a simplified post design is provided. This is composed of a tubular frame which contains two vertical carrying pipes which extend parallel to one another and accept the carriage therebetween and which are connected to one another by a cross-strut at their ends. The two carrying pipes comprise at least one transverse division which roughly halves the tube length, the divided tube sections being connected to one another at this transverse division upon assembly. The guidance elements for the carriage are situated in the carrying pipes.

13 Claims, 2 Drawing Sheets

X-RAY EQUIPMENT SUPPORT APPARATUS

BACKGROUND OF THE INVENTION

1. Field of the Invention

The present invention relates to X-ray diagnostics equipment which are utilized in the field of dental medicine for producing panorama X-rays of the jaw of a patient, and more particularly to a support apparatus for such equipment where it is possible to infinitely adjust the rotatory unit composed of the X-ray generator and X-ray film holder in height in a defined range in order to thus adapt the unit to patients of different sizes (child-/adult) or to different exposure techniques and to heights corresponding to seated or standing positions of a patient.

2. Description of the Prior Art

In equipment of the type described above (brochure M-D 80.1361 ORTHOPANTO-MOGRAPH 10; WS 08832), the rotatory unit is mounted on a carriage which is adjustably held on a stationary post. For reasons of stability, the post is composed of one-piece frame parts having a rectangular cross section and extending practically from floor to ceiling. The running carriage is guided along the narrow sides of the post. The frame parts form a hollow in which weights of steel or lead are arranged via a cable pulley or the like as a weight compensation arrangement for the rotatory unit.

The practically room-high post represents a packaging, transport and handling problem not only because of its length and, thus, bulkiness but also because of its weight. The counter-weight which must be established at about 90 kg also complicates the erection and mounting of the facility. As a consequence of the great weight, an extremely stable and playfree guidance is also required, this involving a corresponding great expenditure of costs.

U.S. Pat. No. 2,369,453 discloses a portable x-ray transillumination apparatus wherein a carrier composed of two-pipes arranged vertically and parallel to one another is pivotably seated on a substructure which is movable by means of rollers. A carriage is height-adjustably arranged on the carrier, a bracket for a luminescent screen and an x-radiator being secured to this carriage. For reasons of packing and assembly, the pipes are composed of three sections, an upper, middle and lower section. A toothed rack is secured to one pipe, this toothed rack being part of the height adjustment means for the carriage.

The pipe sections are connected to one another in antitwist fashion by means of a tappet-sleeve plug connection and by means of a transversely arranged pin which engages into a correspondingly situated groove and the pipes are axially braced relative to one another by means of a tie rod.

Even though more favorable transport and simpler packing can be achieved by means of the cross-division of the pipes, a comparatively involved and time-consuming assembly still is required due to the bracing of the overall pipe structure with the tie rod after the pipes have been plugged together. Further, the toothed rack secured to the outside of the pipe wall as part of the height adjustment means for the carriage is not only aesthetically disturbing but is also unfavorable from a technological point of view since the parts required for the height adjustment means are, first, relatively involved in design and, second, represent an increased contamination hazard.

SUMMARY OF THE INVENTION

The invention is based on an object of providing a mechanism which is improved and simplified in comparison to the device described above with which the cited disadvantages regarding the structure of the post, including the guide parts for the carriage, can be avoided and, in addition, the manufacturing and assembly costs can be reduced.

The length division of the stand pipe advantageously lies in a range between $\frac{1}{3}$ and $\frac{2}{3}$ of the overall length, whereby, first, an acceptable packing size and, second, advantages in fabrication and assembly can be achieved.

BRIEF DESCRIPTION OF THE DRAWINGS

An exemplary embodiment of the invention shall be set forth with reference to the drawings.

Shown therein are.

DESCRIPTION OF THE PREFERRED EMBODIMENTS

Figure 1:
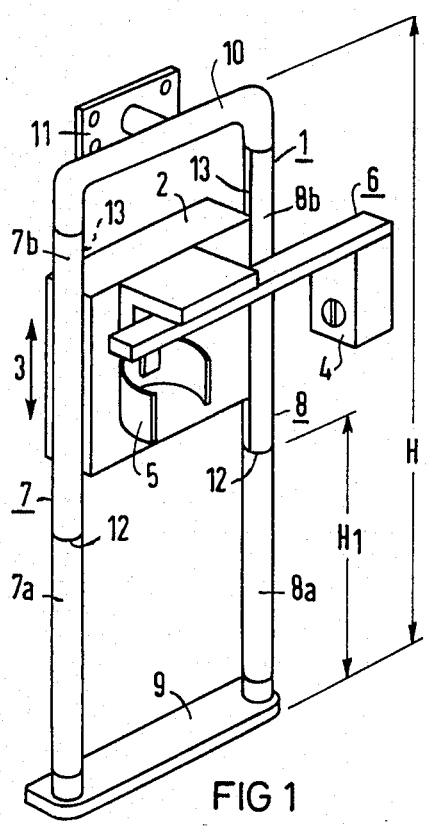
FIG. 1 is a schematic perspective illustration of an apparatus embodying the present invention.

FIG. 1 shows a schematic illustration of a dental x-ray diagnostics installation for producing panorama x-ray pictures. The installation is composed of a post or stand frame member 1 on which a carriage 2 is held adjustable in the direction of the arrow 3. A rotatory unit composed of an x-ray generator 4 and xray film holder 5 is held on the carriage 2 in the usual way. Since the mounting for the rotatory unit is of no significance for the invention, this shall not be set forth in greater detail.

The post 1 is composed of a pipe frame having two parallel, vertical carrying pipes 7, 8 which are connected to one another at their ends with cross-struts 9 and 10. The crossstruts 9, 10 are fashioned U-shaped; the cross-strut 10 at the ceiling side is provided with a spacer member 11 which can be secured to a wall to provide stability to the post 1.

The carrying pipes 7, 8 are transversely divided at the location referenced 12 and can thus be subdivided into two pipe sections, into a lower pipe section comprising stand pipes 7a, 8a and into an upper pipe section comprising pipes 7b, 8b. The pipes of the lower pipe section comprise a closed or circular cross section, whereas the pipes 7b, 8b of the upper pipe section are provided with a longitudinal slot through which parts of a guide means (described below) for the guidance of the carriage project. The transverse division 12 occurs at a location that roughly corresponds to the lowest height adjustment demanded for the rotatory unit 6; calculated from the floor, this height $H_1$ amounts to about 1 m through 1.5 m relative to an overall room height H of about 2.40 m given the setting technique currently standard.

Figure 3:
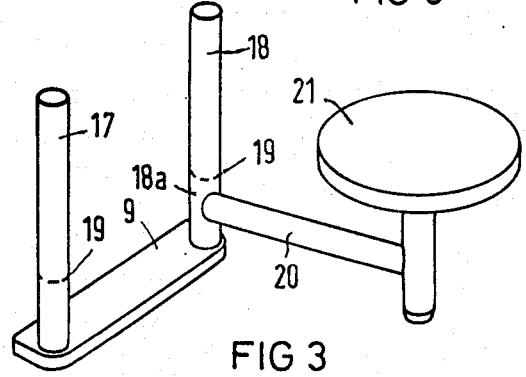
FIG. 3 is a perspective view of an alternative embodiment of a base portion of the apparatus shown in FIG. 1.
Figure 2:
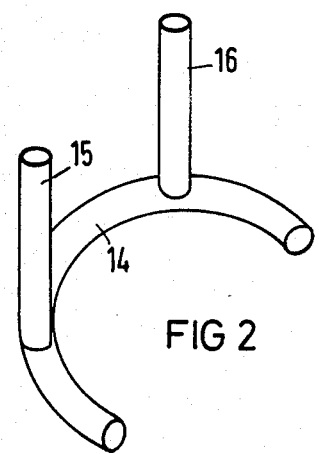
FIG. 2 is a perspective view of an alternative embodiment of a base portion of the apparatus shown in FIG. 1.

As a result of the transverse division of the carrying pipes, it is easily possible to provide a free-standing post unit instead of the post unit attachable to a securing wall or it is also easily possibly to integrate auxiliary equipment such as, for example, a patient chair in the lower pipe section. Two such possibilities are shown in FIGS. 2 and 3. In the one alternative, the foot part shown in FIG. 2 is fabricated with the base 14 bent C-shaped and the two pipes 15 and 16 instead of the lower pipe section comprising the pipes 7a, 8a and the cross-strut 9 (FIG. 1). In the alternative solution of FIG. 3, two stand pipes 17, 18 are again transversely divided at the location referenced 19; a lower pipe part 18a of the stand pipe 18 is provided with an extension arm 20 to which a patient seat 21 is secured. The pipe part 18a is rotatably seated at the cross-strut 9 so that the seat 21 can be pivoted around the bearing axis of the pipe part 18a.

Due to the tubular structure of the post, which is not limited to the employment of cylindrical pipes, as shown, it is possible to offer the user a multitude of different configurations by the use of largely identical structural parts. As a consequence of the transverse division of the vertical carrying pipes into pipes 7a, 7b, 8a and 8b, considerably smaller packing sizes derive in comparison to designs which were previously available.

Figure 4:
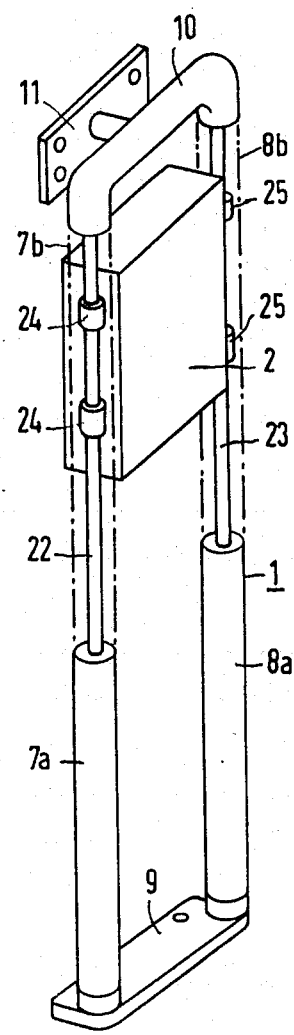
FIG. 4 is a perspective view of the pipe frame structure of FIG. 1 shown by itself.

FIG. 4 shows details of the post structures. The pipes 7b, 8b of the upper pipe section enclose guide rods 22, 23 on which bushings or guide members 24, 25 glide. The bushings 24, 25 are connected to the carriage 2, whereby the bushing 25 is rigidly connected to the carriage 2 and the bushing 24 is loosely connected thereto. Further details may be seen in FIGS. 5 and 6. The guide rods 22, 23 are connected to downwardly directed legs of the upper cross-struts 10 at one end, and at the other end are connected to the pipes 7a, 8a; this connection can expediently consist of a screw-type connection as shown by way of example in FIG. 6.

Figure 5:
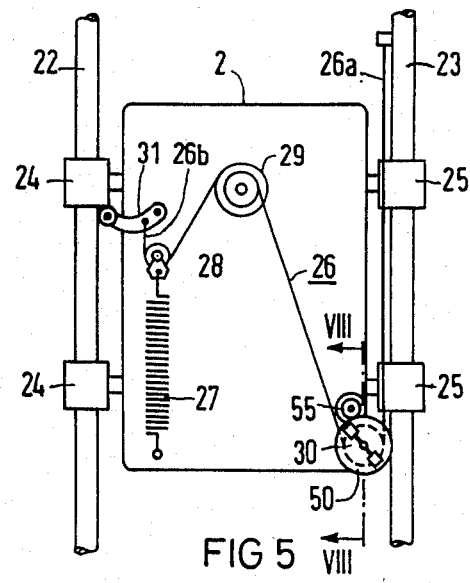
FIG. 5 is a fundamental diagram of the adjustment means of the carriage.

In order to be able to compensate the weight of the rotatory unit 6 secured to the carriage 2, a weight compensation means is provided in the carriage, this weight compensation or counter balancing means being shown on principle in FIG. 5. The compensation means includes a traction cable 26 which is guided via a movably mounted deflection roller 28 loaded by a tension spring 27, via a pulley 29 and via a further deflection roller 30 stationarily mounted on the carriage 2. One end 26a of the traction cable 26 is secured to the guide rod 2 and another end 26b is secured to a clamp means 31. The spring power changing upon dislocation of the carriage is compensated by the pulley 28, so that the weight of the carriage and that of the rotatory unit 6 held thereat is compensated in every height position.

The clamp means 31 is part of a safety brake mechanism that shall be set forth in greater detail with reference to FIG. 6.

As already presented, the carriage 2 is guided in longitudinally displaceable fashion on the guide rods 22, 23 by means of the guide bushings 24, 25. To this end, FIG. 6 shows the left part of the guidance arrangement in greater detail. A ball bearing bushing is provided as the guide bushing 24, a pin 33 which is rigidly connected to a frame 34 of the carriage 2 being secured thereto. The connection is loose at the pin side, and, thus, the ball bearing bushing 24 can move slightly there in an axial direction of the pin 33 toward the frame 34, whereby a tilting of the carriage on the guide rods 22, 23 is avoided.

The guide bushing 24 contains a wedge 35 provided with a slanting surface with which a pinch roller 36 interacts. The pinch roller 36 is secured to a rocker arm 37 which is in turn tiltably secured to the frame 34 by means of bearing or pivot arm 38. The one end 26b of the traction cable 26 is attached to the rocker arm 37. Given the tension on the cable 26 which is normally present, the rocker arm 37 is pressed against a detent 39 in the frame 34. In this position, the roller 36 does not have any contact with the guide rod 22. If the cable tension is reduced, the pinch roller 36 will be seized between the slant of the wedge 35 and the guide rod 22 upon a downward movement of the overall carriage due to the lack of cable tension, whereby the carriage will be is immediately arrested. A tension spring 32 arranged between frame 34 and rocker arm 37 will promote the seizing operation upon the occurrance of cable breakage.

It may be seen when viewing FIG. 5 that the cable 26 is conducted over the two guide bushings 25 proceeding from the deflection roller 30. Corresponding clearances in the form of, for example, recesses, passages or slots are provided for this purpose, as referenced with numeral 40 in FIG. 6.

Figure 6:
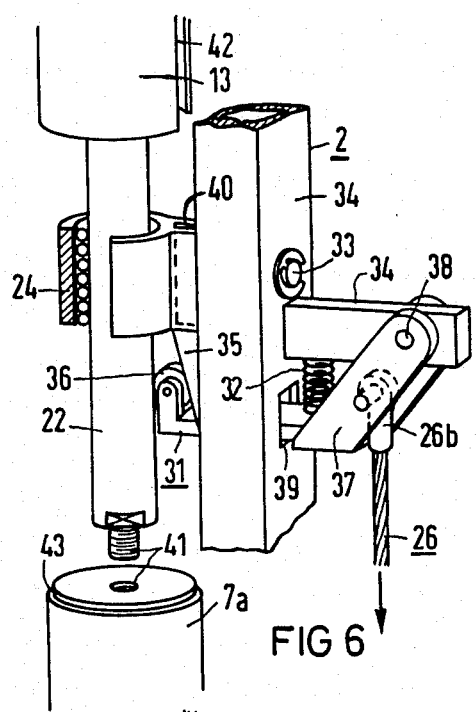
FIG. 6 is a partial perspective view of the details relating to the structure and assembly of the pipe structure and of a safety lock mechanism for the carriage.

The connection of the guide rod 22 to the carrying pipes 7a of the lower pipe section is also shown in FIG. 6. Some other adequate connection can also be provided instead of the screwtype connection illustrated which is composed of a threaded trunnion and threaded bore.

In the region of the pipe sections 7b, 8b, the guide means is surrounded by an outer cladding 42 containing the longitudinal slot 13. This cladding shown at the upper left in FIG. 6 is centered by a small shoulder 43 in the corresponding carrying pipe.

Figure 7:
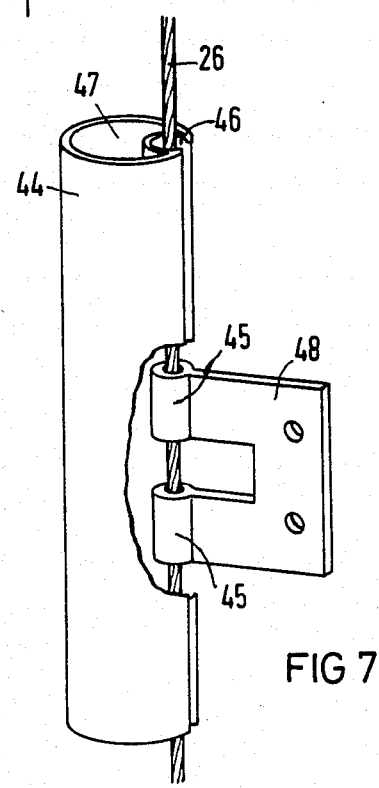
FIG. 7 is a perspective view of an alternative solution for the guidance of the carriage.

The cladding 42 can be fabricated of a rolled sheet metal panel. In accord with an advantageous embodiment of the invention, however, it can also be fashioned such that it also forms the bearing for the guidance of the carriage. Such an alternative solution is shown in FIG. 7. Cladding and stand pipe herein are composed of a part 44 rolled in accord with the illustrated profile. The profile is shaped such that a cylindrical guide channel 46 corresponding to guidance parts 45 is formed. The remaining cavity 47 can be filled with foam, whereby the guide channel 46 is given additional stiffness. In this alternative solution, the carriage is secured to a carrier part 48 connected to the guidance parts 45. The guidance parts 45 are advantageously designed as bushings for the guidance of the traction cable.

Figure 8:
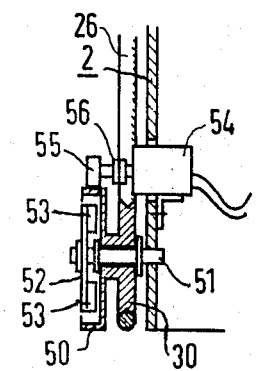
FIG. 8 is a sectional view generally taken along the line VIII—VIII of FIG. 5.

As may be seen from FIG. 8 which shows a section along the line VIII—VIII in FIG. 5, the deflection roller 30 is connected to a pot-like drum 50 of low-magnetic retentivity material. Drum 50 and deflection roller 30 are rotatably mounted on a shaft 51 secured to the carriage 2. A lever 52 is secured to the shaft 51, two electromagnetic coils 53 being arranged at this lever 52. Together with the drum 50, these coils form an electro magnetic brake which serves the purpose of retaining the carriage 2, and, thus, the rotatory unit 6 carried by the carriage 2, in an arbitrarily adjustable height position. The engagement and disengagement of the two pot magnets 53 can ensue in a known way by a switch or key arranged in a circuit (not shown).

The drum 50 also serves for the motor driven displacement of the carriage 2. To this end, a friction wheel 55 driven by an electric motor 54 lies against the outside drum edge. A friction clutch 56 arranged between drive motor 54 and friction wheel also allows a manual adjustment of the carriage.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. In a dental medical apparatus including a stationarily erectible post on which a carriage is adjustably held by means of a guide device, said carriage being the carrier of a medical apparatus, being a rotatory unit composed of an X-ray generator and X-ray film holder, said post being formed of a tubular frame which contains two vertical carrying pipes which proceed parallel to one another and accept said carriage therebetween, said carrying pipes being connected to one another at least at their ends by means of a cross-strutting and comprising at least one transverse division within the pipe length at which the divided pipe sections are joined to one another during assembly, the improvement comprising both of said carrying pipes being composed of a lower pipe section at the floor side which extends up to said transverse division and includes pipes having a closed cross section, and being composed of an upper pipe section above and connected to said lower pipe section and including pipes having a cross section open at one side and thus forming a profile having a longitudinal slot; and said upper pipe section containing guide elements for an adjustment of said carriage arranged between said carrying pipes of said upper pipe section.

2. An apparatus according to claim 1, wherein said guide elements for said guidance of said carriage are rigidly connected to said carriage at one side of said carriage and are loosely connected thereto at the other side of said carriage.

3. An apparatus according to claim 1, wherein said pipes of said pipe section provided with longitudinal slots are formed by a cladding tube which is shaped such that it forms a guide channel and a guidance part secured to said carriage glidingly receivable in said guide channel.

4. An apparatus according to claim 3, wherein said cladding tube is fabricated of a rolled sheet metal panel.

5. An apparatus according to claim 1, wherein said pipes of said pipe section provided with said longitudinal slot each contain a centrally arranged guide rod, which is connectible to the frame at an upper and lower end, guide bushings connected to said carriage for gliding along said guide rod; and both said guide rods surrounded by a cladding tube containing said longitudinal slot and corresponding in outside diameter to the parts adjoining thereto.

6. An apparatus according to claim 5, wherein said cladding tube is fabricated of a rolled sheet metal panel.

7. An apparatus according to claim 2, wherein a spring weight compensation means is provided on said carriage, said spring weight compensation means comprising a tension spring and a traction cable guided via deflection rollers and a cable cam, one end of said traction cable being secured to one of said guide rods in said tubular frame and the other end thereof being secured to said carriage.

8. An apparatus according to claim 7, wherein said carriage is provided with a safety brake means which is comprised of a pinch member connected to one end of said traction cable and pinchable between said guide rod and a slanting surface connected to said carriage, said pinch member coming into engaged pinch position as a consequence of the spring effect of said tension spring upon a lack of cable tension and coming into its unengaged position upon a predetermined level of cable tension.

9. An apparatus according to claim 1, wherein said two carrying pipes are connected to one another by means of cross-struts designed U-shaped and contain connecting elements for an easy connection to said carrying pipes, said cross-struts containing said connecting elements at their ends which define the spacing of said carrying pipes.

10. An apparatus according to claim 9, wherein a pivotable arm comprising a patient seat is held at the pipe section connected to the cross-strut at a lower end.

11. An apparatus according to claim 10, wherein said arm is secured to a pipe element formed by a further transverse division and said further transverse division is also present at the opposite pipe of the pipe section upon formation of equal pipe lengths.

12. An apparatus according to claim 9, wherein said cross-strutting at said lower end forms a base preferably fashioned C-shaped which carries said facility in free standing fashion.

13. An apparatus according to claim 9, wherein a supporting element fixing a distance to a securing wall is provided at said upper cross-strut.

* * * * *